(12) United States Patent
Knoeller

(10) Patent No.: US 9,380,852 B2
(45) Date of Patent: Jul. 5, 2016

(54) LACQUER CRAYON

(71) Applicant: M. Heyer GmbH Applikator-Systeme, Markt Erlbach-Eschbach (DE)

(72) Inventor: Petra Knoeller, Stuttgart (DE)

(73) Assignee: M. Heyer GmbH Applikator-Systeme, Markt Erlbach-Eschbach (DE)

( * ) Notice: Subject to any disclaimer, the term of this patent is extended or adjusted under 35 U.S.C. 154(b) by 172 days.

(21) Appl. No.: 14/365,327

(22) PCT Filed: Dec. 14, 2012

(86) PCT No.: PCT/EP2012/075533
§ 371 (c)(1),
(2) Date: Jul. 2, 2014

(87) PCT Pub. No.: WO2013/087836
PCT Pub. Date: Jun. 20, 2013

(65) Prior Publication Data
US 2014/0328612 A1 Nov. 6, 2014

(30) Foreign Application Priority Data
Dec. 14, 2011 (DE) .......................... 10 2011 120 943

(51) Int. Cl.
| | | |
|---|---|---|
| A45D 34/04 | (2006.01) | |
| A61K 8/25 | (2006.01) | |
| A61K 8/33 | (2006.01) | |
| A61K 8/37 | (2006.01) | |
| A61Q 3/02 | (2006.01) | |
| A61K 8/73 | (2006.01) | |
| A45D 40/20 | (2006.01) | |

(52) U.S. Cl.
CPC .............. *A45D 34/042* (2013.01); *A45D 34/04* (2013.01); *A45D 40/20* (2013.01); *A61K 8/25* (2013.01); *A61K 8/33* (2013.01); *A61K 8/37* (2013.01); *A61K 8/731* (2013.01); *A61Q 3/02* (2013.01); *A61K 2800/872* (2013.01)

(58) Field of Classification Search
CPC combination set(s) only.
See application file for complete search history.

(56) References Cited

U.S. PATENT DOCUMENTS

| | | | |
|---|---|---|---|
| 4,747,419 A | | 5/1988 | Flynn et al. |
| 4,936,700 A | * | 6/1990 | Morris ................... A45D 34/04 215/348 |
| 6,883,995 B1 | | 4/2005 | Gueret |
| 8,282,302 B2 | * | 10/2012 | Zahn ...................... B43K 23/12 401/196 |
| 2007/0207096 A1 | | 9/2007 | Puisset et al. |

FOREIGN PATENT DOCUMENTS

EP    1 094 011 A1    4/2001

OTHER PUBLICATIONS

Material Safety Data Sheet, Methyl Ethyl Ketone, Sasol, Mar. 28, 2007, pp. 1-7.
Product Information n-Butyl Acetate, The Dow Chemical Company, Oct. 2002 (2 pages).
Material Safety Data Sheet, 1-Methoxy-2-propanol, Edwards, Nov. 2007 (7 pages).
International Search Report in PCT/EP2012/075533, dated Aug. 6, 2014.

* cited by examiner

*Primary Examiner* — David Walczak
(74) *Attorney, Agent, or Firm* — Collard & Roe, P.C.

(57) ABSTRACT

A lacquer crayon includes a nail varnish having 20-40 wt % of a lacquer component which includes a swellable layer silicate or a derivative thereof, dissolved and/or dispersed in 60-85 wt % of a substantially waterless solvent mixture which is composed of 10-30 wt % of low-boiling components, 20-50 wt % of medium-boiling components, 20-50 wt % of high-boiling components based on 100 wt % of solvent mixture, in such a way that the lacquer component and the solvent mixture add up to 100 wt %, wherein the lacquer crayon includes a reservoir for the lacquer, a valve, a tip made of an extruded or fibrous material and a removable cap which includes a moisture retaining element.

16 Claims, 1 Drawing Sheet

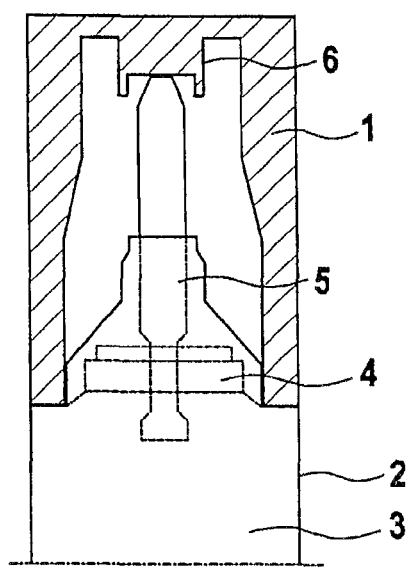

LACQUER CRAYON

CROSS REFERENCE TO RELATED APPLICATIONS

This application is the National Stage of PCT/EP2012/075533 filed on Dec. 14, 2012 which claims priority under 35 U.S.C. §119 of German Application No. 10 2011 120 943.7 filed on Dec. 14, 2011, the disclosure of which is incorporated by reference. The international application under PCT article 21(2) was not published in English.

The invention relates to a nail polish pen that contains a nail polish composed of a lacquer component and a solvent mixture, wherein the nail polish pen has a reservoir for the nail polish, a valve, a tip composed of an extruded or fibrous material, a removable cap, and a moisture-retention element containing a humectant in the cap.

Such nail polish pens are currently produced predominantly on the basis of water, i.e. the lacquer components are dispersed in an aqueous solvent. They are referred to in the art as French manicure pens or as French liners or as nail art pens. The disadvantage of these pens is the insufficient durability on the fingernails (due to water as the solvent) and the restricted selection of film-forming agents and polymers also due to this, as well as the dull appearance of the applied varnish film. These nail polishes require the use of commercially available topcoats, which then allow a durability of two, maximally three days on the fingernails.

Such lacquers based on water generally have a dynamic viscosity between 20 and 150 mPas, are adjusted to have little or no thixotropicity, and have surface tensions of clearly greater than 40 mN/m.

Nail polishes, both colors and clear polishes, along with topcoats and nail polish removers, generally contain ethyl acetate and butyl acetate. These solvents have a good dissolution behavior with regard to usual film-forming agents and viscosity regulators. For this reason, topcoats, particularly what are called quick dry topcoats having a high proportion of solvent, always dissolve part of a layer of dried nail polish when applied to it.

In the case of commercially available nail polishes that have a high dynamic viscosity (in the non-shaken state>2,000 mPas, in the shaken state>600 mPas) and form a sufficiently thick layer on the nail also because of being applied with a brush, this partial dissolution is not problematic and does not bring with it any disadvantages during application.

This is different in the case of application using a nail polish pen. The nail polishes contained in nail polish pens are adjusted to be clearly lower with regard to their dynamic viscosity, in order to allow the nail polish to flow through the valve and the tip. The resulting layer thickness on the nail is therefore much less than in the case of normal nail polish. Application of a topcoat to the nail polish applied using the French manicure nail polish pen therefore dissolves this layer again to a not insignificant extent, and this results in "smearing" of the nail polish.

When used as nail art, in other words when applying a nail polish to a layer of polish that has already dried, conventional nail polishes partly dissolve the polish layer to which polish is being applied, because the solvents used are the same as those of the lower layer. This results in smearing and in a not insignificant discoloration of the brush/the application aid.

A number of requirements for a nail polish pen of the type stated initially result from this situation and from practice.

The nail polish should have a durability of at least four days on the fingernail, when using a commercially available long-lasting topcoat. It should also be adjusted in terms of elasticity in such a manner that it does not chip or split off.

It should be possible to cover the nail polish with any commercially available long-lasting topcoat, both with a colorless long-lasting topcoat that is brushed on once, and with a rose-colored or beige-colored French nail polish, which is applied maximally three times, without any smearing, in each instance.

The nail polish should dry at least as quickly as a usual water-based system.

The nail polish should allow establishing a three-dimensional film structure during the drying time.

The nail polish is not allowed to dry out in the tip of the nail polish pen.

It must be possible to distribute the nail polish uniformly on the nail, particularly at the edge of the nail, without forming stripes.

The nail polish must flow out of the reservoir well.

It must be possible to activate the pen sufficiently quickly.

The nail polish must have sufficient adhesion capacity.

The viscosity of the nail polish should be adjusted in such a manner that sufficient flow behavior through the valve of the nail polish pen and the tip exists, but on the other hand, pigment sedimentation takes place only very slowly.

When used as a nail art pen, the nail polish in question must partly dissolve a lower nail polish layer that has already dried, only to the most minimally possible extent, in order to prevent smearing or discoloration of the tip used.

These requirements are met by a nail polish pen that contains a nail polish with 20-40 wt. % of a lacquer component that contains an expandable sheet silicate or derivative thereof, dissolved and/or dispersed in 60-85 wt. % of an essentially anhydrous solvent mixture, which is composed of 10-30 wt. % components with a low boiling point,
20-50 wt. % components with a medium boiling point,
20-50 wt. % components with a high boiling point, with reference to 100 wt. % solvent mixture, in such a manner that the lacquer component and the solvent mixture add up to 100 wt. %, wherein the nail polish pen has a reservoir for the nail polish, a valve, a tip composed of an extruded or fibrous material, and a removable cap that contains a moisture-retention element.

The nail polish pen according to the invention offers longer durability on the nail and greater shine than water-based lacquers used until now, by means of the use of corresponding film-forming agents, copolymers, and plasticizers. As a solvent-based nail polish, it does not represent a substrate for microorganisms. Production is simpler than in the case of aqueous systems, on the basis of the greater compatibility of the components.

The nail polish used in the nail polish pen according to the invention is a pigmented or colored dispersion of the lacquer components in a solvent mixture of the stated type. The dynamic viscosity lies in a range of 20 to 300 mPas (Haake 20° C.), and particularly from 80 to 130 mPas, at a surface tension in the range of 15 to 30 mN/m, and particularly about 20 to 25 mN/m. Silicon oil or derivatives thereof can be contained in it to adjust the surface tension.

It is understood that the term "lacquer component" according to the invention includes all the constituents of the actual lacquer, without solvent, in other words not only pigment, film-forming agent, and binders, but also usual suspension agents, viscosity regulators, dispersion aids, plasticizers, active substances for nail care, and the like. The solvent categories as defined further below are contained in the solvent mixture.

In the cosmetics industry, sheet silicates or their derivatives have proven themselves as pigment substances and structure substances. These are, above all, bentonites and montmorillonites. However, it has been shown that a preparation on the basis of hectorite is particularly suitable for purposes according to the invention. This provides very good stability and an acceptable flow behavior of the lacquer.

A proven pigment preparation is a stearalkonium hectorite, as it is used, for example, under the trade name Hacorit® in combination with nitrocellulose. Hacorit contains hectorite, which is superior, in terms of being worked in, to other sheet silicates usually used, because of its very great surface area, good gel formation properties, and the absence of crystalline silicon dioxide. As stearalkonium hectorite, it can also be dispersed well in solvent mixtures. Hectorite forms a three-dimensional "house of cards" structure in the dry nail polish film, which results in good resistance to dissolution effects of the topcoat and a delay in sedimentation in the lacquer. The same holds true for stearalkonium bentonite, particularly Tixogel LG-M®, which is characterized by improved swelling behavior and the ability to be worked into highly polar solvents.

Stearalkonium hectorite, sold under the Hacorit trade name, contains not only nitrocellulose but also acetyl tributyl citrate as a suspension agent. The preparation can be dispersed in a solvent mixture of ethyl acetate (or higher carboxylic acids) and ethanol (90:10 to 50:50), using usual aids, in simple manner, and this dispersion can be introduced into the lacquer preparation.

Organophilic bentonites also serve as thixotropic thickening agents in polar solvents; these agents prevent settling of inorganic pigments and floating of organic pigments to the top. They furthermore impart a certain color brilliance to the lacquer. The combination of stearalkonium bentonite with propylene carbonate is particularly suitable for bringing about such an effect. Analogously, citric acid or phosphoric acid can also be used for this purpose.

Furthermore, the nail polishes described here can contain usual pigments, for example $TiO_2$, organic coloring agents, and varnishes. It is practical if the content in the nail polish is about 5 to 25 wt. %.

It has proven to be advantageous to use a mixture of a nitrocellulose with medium to high viscosity (standard type E15) and a nitrocellulose with normal viscosity (standard type E22) for the nitrocellulose contained in the lacquer component. The ratio preferably lies in the range of 1:6 to 1:1, and particularly at a ratio of about 1:3.

Similarly suitable and preferred is a nitrocellulose with medium viscosity, of the A type. Nitrocelluloses of the A type generally dissolve well in alcohol.

The nitrocellulose brings about excellent film formation, but also contributes to the drying behavior and to the flowability during application. The nitrocellulose concentration lies at 1 to 12 wt. % of the nail polish.

In order to impart the necessary elasticity to the nail polish film, it is practical to mix in plasticizers. Citrates, particularly acetyl tributyl citrate, which is also helpful in the formulation of the hectorite component, have proven to be particularly compatible with the lacquer according to the invention, as have various branched resins, for example those copolymers formed from adipic acid, neopentyl glycol, and trimellitic anhydride, which also fulfill a binder function. It is practical if the citrates are contained in an amount of 3 to 8 wt. %, and the copolymers are contained in an amount of 0.1 to 7 wt. %, with reference to the lacquer, in each instance.

The sheet silicate is usually contained in the nail polish in an amount of 0.5 to 5 wt. %. The solvent composition is of particular importance both for the flow behavior and for the drying behavior. The solvents used in usual nail polishes and removers, ethyl acetate and butyl acetate, dry very quickly on the nail in a thin layer. In this way, a correction of the line drawn is therefore not possible, in most cases. Furthermore, however, the drying behavior also appears to have an influence on establishing the three-dimensional structure of the sheet silicate. For this reason, a mixture of solvents that yields an optimum in terms of drying time but, at the same time, also takes the flow behavior of the nail polish in the pen during application, and the three-dimension build-up of the structure into consideration, was developed. In this connection, vapor pressure, boiling points, and evaporation numbers of the individual solvents were included in deliberations.

An optimal mixture ratio that also takes the solubilities of the individual raw materials and the boundary surface tensions and final viscosity of the dissolved nitrocellulose into consideration lies at a proportion of 10-30 wt. % components with a low boiling point, 20-50 wt. % components with a medium boiling point, and 20-50 wt. % components with a high boiling point, with reference to the total solvent mixture, in each instance.

Components with a low boiling point generally have a boiling point less than 80° C., components with a medium boiling point one in the range of 80 to <120° C., and components with a high boiling point one of more than 120° C. Typical components with a low boiling point are ethyl acetate and ethanol; typical components with a medium boiling point are propanol, isopropanol, butyl acetate, and isopropyl acetate; typical components with a high boiling point are methoxyisopropyl acetate, methoxyisopropanol, and propylene carbonate.

Preferably, the proportion of ethanol in the solvent mixture amounts to 10 to 30 wt. %, that of methoxyisopropanol to 20 to 40 wt. %, and that of propylene carbonate to 2 to 10 wt. %.

In general, alcohols usual in the cosmetics industry, with up to 4 carbon atoms, acetic acid esters with an alcohol with up to 4 carbon atoms, as well as single-methoxylated or multiple-methoxylated derivatives of these compounds can be used for the components with a low, medium, or high boiling point.

In the solvent according to the invention, the use of ethanol, propanol, and isopropanol, on the one hand, and of methoxypropanol, on the other hand, is particularly preferred. The lower alcohols, particularly ethanol, demonstrate good dissolution capacity for the nitrocellulose. Methoxypropanol, on the other hand, is suitable for drawing the boiling point of the solvent mixture upward and thereby for preventing overly rapid drying and also drying-out of the pen. Furthermore, methoxypropanol also imparts particularly good flow properties and running properties to the nail polish.

The nail polishes contained in the nail polish pens according to the invention require a boundary surface tension that lies above that of the plastic material used for the nail polish pen tip, in order to achieve acceptable flow behavior at the tip. The cohesion must be less than the adhesion. At the same time, the boundary surface tension should be as low as possible, in order to allow rapid activation of the pen. This is achieved by the solvent mixture. This mixture particularly has a boundary surface tension in the range of 15 to 30 mN/m and, in particular, one in the range of 20 to 25 mN/m.

In the case of the solvent mixtures according to the invention, tips made from extruded polypropylene or from a fibrous or fiber-type acrylic material demonstrate the best application properties. Furthermore, polyester tips are suitable. The essential thing is that the fiber material demonstrates good capillarity and thereby guarantees sufficient flow of the nail polish material during application.

The nail polish pens with the nail polishes specified above are those of a usual type, i.e. they consist of a reservoir, an application tip, and a tightly sealing cap. In addition, there can be a pump mechanism to bring about conveying of the nail polish material from the reservoir to the application tip. Such pump mechanisms are also known.

However, a problem with nail polishes based on solvents, in nail polish pens, is their tendency to dry out. After first-time activation of the pen, the tip threatens to dry out in the cap and to become glued up with the lacquer components contained in it. In order to prevent this, it is provided, according to the invention, to introduce a moisture-retention element into the cap, particularly into the end of the cap. Such a moisture-retention element is, for example, an absorbent polymer that can hold a large amount of humectant, particularly about 3 to 8 times the inherent weight of the polymer. A suitable polymer is a sponge, particularly one composed of nitrile rubber (NBR).

A preferred variant of the moisture-retention element is an accommodation for the application tip that is disposed in the end of the cap. This accommodation can contain a sponge-like element, but this is not necessary. It is sufficient if the cap, in the closed state, presses the application tip into the valve with the accommodation, and thereby holds the valve slightly open. The diffusion stream of nail polish material triggered in this way is sufficient to keep the application tip moist and ready for use. In particular, such an accommodation is an insert in the cap that is molded onto the end of the cap or molded out of it.

The accommodation for the application tip can closely surround the tip, but this is not necessary. It is important that when the pen is closed, the accommodation presses the tip into the valve slightly. As a result, the valve opens slightly; because of capillarity or due to flow channels contained in the tip, the tip is constantly supplied with nail polish and therefore cannot dry out. On the other hand, the valve is only activated slightly, so that the pen cannot run out. The presence of components with a medium and a high boiling point in the solvent mixture is also suitable for counteracting drying out.

The humectant, if present, in the moisture-retention element should have a sufficiently high evaporation number to prevent drying out over the useful lifetime of the pen. The evaporation number should lie in the range of 20 to 40, particularly it should be >25. Methyl isopropyl acetate has an evaporation number of 34 and is therefore suitable.

The evaporation number is assumed to be a multiple of the evaporation time that a substance requires, in comparison with diethyl ether, in order to evaporate completely. The evaporation number of diethyl ether is 1. A substance with the evaporation number 33 therefore requires 33 times as much time to evaporate completely.

In particular, the solvent mixture used for the nail polish, or the nail polish itself, which consists of solvent mixture to a high percentage, is a possible humectant in the moisture-retention element. However, the use of a solvent with an evaporation number>25, particularly of methoxyisopropyl acetate, also with the addition of further humectants, e.g. ethylene glycol, is preferred.

Furthermore, a usual polymer is used for the nail polish pen according to the invention; it is required that this polymer is essentially impermeable for the solvent mixture of the nail polish and resistant to it. PP, PET, PBT, PA, and PC, for example, are suitable. The same holds true analogously for the valve for metering. The polymers are generally thermoplastic polymers.

The invention will be explained using the following examples.

EXAMPLE 1

A nail polish was produced from

| Component | Proportion in wt.-% |
|---|---|
| ethyl acetate | up to 100 |
| methoxyisopropanol | 15.0 |
| methoxyisopropyl acetate | 14.0 |
| butyl acetate | 10.0 |
| denatured alcohol | 4.8 |
| isopropyl alcohol | 1.5 |
| $TiO_2$ | 10.0 |
| nitrocellulose mixture | 5.8 |
| acetyl tributyl citrate | 5.8 |
| copolymer | 3.14 |
| stearalkonium hectorite | 1.7 |

For production, a dispersion of stearalkonium hectorite, acetyl tributyl citrate, and nitrocellulose was produced in a mixture of alcohol and isopropyl alcohol. This mixture was stirred into the mixture of the other solvents. The copolymer and the titanium dioxide were stirred into this mixture; this mixture was then filled into nail polish pens after filtration.

EXAMPLE 2

A nail polish was produced from

| methoxyisopropanol | up to 100% |
|---|---|
| denatured alcohol | 23.8% |
| titanium dioxide | 20.0% |
| acetyl tributyl citrate | 6.5% |
| nitrocellulose, Type A | 6.2% |
| propylene carbonate | 4.0% |
| isopropyl alcohol | 4.5% |
| stearalkonium bentonite | 0.9% |

Production of the nail polish took place as indicated in Example 1.

The nail polishes used according to the invention have greater durability than the known water-based nail polishes in corresponding pens. Because of the use of nitrocellulose, the adhesion is also clearly improved, as compared with water-based nail polishes. Thus, it is easily possible to apply the nail polishes described here directly to the nail, or also to apply them to nails that have already been polished, as nail art. The solvent mixture is adjusted in such a manner that the nail polish layers underneath are hardly partially dissolved at all, and are not smeared. The nail polishes furthermore have great covering power. The drying time is generally shorter than in the case of water-based nail polishes—also because of the use of components with a low boiling point in the solvent mixture. Because of the relatively slight surface tension, the flow behavior is uniform, and the undesirable contraction of the lines during application does not take place.

In the attached figure, the cap that can be used according to the invention, with the moisture-retention element, can be seen. The cap 1 is set onto the pen 2 with the nail polish reservoir 3 and the valve 4. The application tip 5 penetrates through the valve 4. The valve itself is elastic and suitable for opening when pressure is exerted on the application tip, and dispensing nail polish from the reservoir 3. In the pressure-free state, the valve 4 is closed.

In the cap 1, an accommodation 6 is molded onto the cap end, against which the application tip 5 bumps up when the cap is closed. In this connection, the accommodation exerts pressure on the application tip. This ensures a slight flow of nail polish from the reservoir through the fiber material (capillarity) into the application tip. The tip therefore does not dry out.

The accommodation itself can be restricted to representing a contact point for the application tip, but can also enclose the application tip, at least in the outer region, to a greater or lesser degree.

The invention claimed is:

1. Nail polish pen, containing a nail polish with
   20-40 wt. % of a lacquer component that contains an expandable sheet silicate or derivative thereof, dissolved and/or dispersed in
   60-85 wt. % of an essentially anhydrous solvent mixture, which is composed of
   10-30 wt. % components with a low boiling point,
   20-50 wt. % components with a medium boiling point,
   20-50 wt. % components with a high boiling point,
   with reference to 100 wt. % solvent mixture, in such a manner that the lacquer component and the solvent mixture add up to 100 wt. %,
   wherein the nail polish pen has a reservoir for the nail polish, a valve, a tip composed of an extruded or fibrous material, a removable cap, and a moisture-retention element containing a humectant.

2. Nail polish pen according to claim 1, wherein the moisture-retention element is an accommodation for a tip.

3. Nail polish pen according to claim 1, wherein the moisture-retention element is an insert in the cap that presses the tip into the valve when the pen is closed.

4. Nail polish pen according to claim 3, wherein the insert is an accommodation for the tip, molded out of the cap.

5. Nail polish pen according to claim 1, wherein the moisture-retention element is an absorbent cushion that is saturated with the humectant.

6. Nail polish pen according to claim 5, wherein the moisture-retention element contains the solvent mixture of the nail polish.

7. Nail polish pen according to claim 1, wherein the moisture-retention element contains a solvent with an evaporation number of >25 as the humectant.

8. Nail polish pen according to claim 1, wherein the tip comprises extruded plastic or plastic fibers.

9. Nail polish pen according to claim 8, wherein the tip comprises polypropylene fibers, acrylic fibers, methacrylic fibers or polyester fibers.

10. Nail polish pen according to claim 1, wherein the lacquer component contains 0.2-5 wt. % sheet silicate, with reference to the nail polish.

11. Nail polish pen according to claim 10, wherein the sheet silicate is stearalkonium bentonite.

12. Nail polish pen according to claim 1, wherein the lacquer component contains 1-12 wt. % nitrocellulose, with reference to the total nail polish, as a film-forming agent.

13. Nail polish pen according to claim 12, wherein the solvent mixture contains 20 to 40 wt. % methoxyisopropanol.

14. Nail polish pen according to claim 1, wherein the solvent mixture contains 2 to 10 wt. % propylene carbonate.

15. Nail polish pen according to claim 1, wherein the lacquer component contains 2.5 to 15 wt. % plasticizing constituents, with reference to the nail polish.

16. Nail polish pen according to claim 15, wherein the plasticizing constituents are acetyl tributyl citrate and/or a copolymer of adipic acid, neopentyl glycol, and trimellitic acid anhydride.

* * * * *